US010836790B1

(12) United States Patent
Zurlo et al.

(10) Patent No.: US 10,836,790 B1
(45) Date of Patent: Nov. 17, 2020

(54) THERAPEUTIC PROTEIN COMPOSITIONS AND METHODS

(71) Applicant: PLASMA TECHNOLOGIES, LLC, Charleston, SC (US)

(72) Inventors: Eugene Zurlo, Charleston, SC (US); Dennis Curtin, Plattsburgh, NY (US); Peter Radtke, Charleston, SC (US); Kurt L. Brillhart, Mission Viejo, CA (US)

(73) Assignee: Plasma Technologies, LLC, Charleston, SC (US)

( * ) Notice: Subject to any disclaimer, the term of this patent is extended or adjusted under 35 U.S.C. 154(b) by 0 days.

(21) Appl. No.: 16/740,286

(22) Filed: Jan. 10, 2020

Related U.S. Application Data

(60) Provisional application No. 62/903,659, filed on Sep. 20, 2019.

(51) Int. Cl.
| | |
|---|---|
| *C07K 1/30* | (2006.01) |
| *G01N 30/12* | (2006.01) |
| *G01N 30/06* | (2006.01) |
| *G01N 1/40* | (2006.01) |
| *C07K 1/36* | (2006.01) |
| *G01N 33/49* | (2006.01) |
| *C07K 1/16* | (2006.01) |
| *C07K 14/76* | (2006.01) |

(52) U.S. Cl.
CPC ............... *C07K 1/16* (2013.01); *C07K 1/30* (2013.01); *C07K 1/36* (2013.01); *C07K 14/76* (2013.01); *G01N 1/40* (2013.01); *G01N 1/4055* (2013.01); *G01N 30/06* (2013.01); *G01N 30/12* (2013.01); *G01N 33/491* (2013.01)

(58) Field of Classification Search
CPC . C07K 1/16; C07K 1/18; C07K 1/122; C07K 1/32; C07K 1/303; C07K 1/30; C07K 1/34; C07K 1/36; C07K 14/8125; C07K 14/128; C07K 16/00; G01N 33/491; G01N 30/04; G01N 30/06; G01N 230/062; G01N 230/065; G01N 230/14; G01N 1/28; G01N 1/40; G01N 1/4055; G01N 1/34; G01N 2001/4061; G01N 2001/4066; G01N 2001/4088; G01N 2001/4083; B01D 15/38; B01D 15/3804; B01D 15/3809; B01D 15/3823; B01D 15/12; B01D 15/125; B01D 11/04; B01D 11/0492

See application file for complete search history.

(56) References Cited

U.S. PATENT DOCUMENTS

| | | | | |
|---|---|---|---|---|
| 4,086,218 A | * | 4/1978 | Shanbrom | A01N 1/02 530/383 |
| 4,305,871 A | * | 12/1981 | Shanbrom | A61K 35/16 530/383 |
| 4,321,192 A | * | 3/1982 | Jain | A23C 9/144 128/DIG. 22 |
| 4,639,513 A | * | 1/1987 | Hou | B01J 20/3217 424/177.1 |
| 4,678,566 A | * | 7/1987 | Watanabe | A61M 1/3472 210/143 |
| 5,420,250 A | | 5/1995 | Lontz | |
| 5,817,765 A | * | 10/1998 | Isaksson | C07K 1/14 530/364 |
| 6,541,518 B2 | * | 4/2003 | Shanbrom | A61P 43/00 514/557 |
| 6,835,379 B2 | * | 12/2004 | Andersson | C07K 16/065 424/130.1 |
| 8,329,878 B2 | | 12/2012 | Randolph | |
| 2003/0129167 A1 | | 7/2003 | Shanbrom | |
| 2005/0196393 A1 | * | 9/2005 | Shanbrom | A61K 31/57 424/94.64 |
| 2007/0049732 A1 | * | 3/2007 | Zurlo | C07K 14/765 530/387.1 |
| 2007/0049734 A1 | * | 3/2007 | Zurlo | A61M 1/3486 530/387.1 |
| 2010/0145021 A1 | | 6/2010 | Marguerre | |
| 2011/0091992 A1 | * | 4/2011 | Dall'Acqua | C07K 16/2866 436/501 |
| 2011/0152503 A1 | * | 6/2011 | Zurlo | A61K 38/57 530/369 |
| 2018/0306772 A1 | * | 10/2018 | Zurlo | C07K 1/22 |
| 2019/0055282 A1 | * | 2/2019 | Zurlo | B01D 61/145 |

FOREIGN PATENT DOCUMENTS

EP      1928915      3/2007

OTHER PUBLICATIONS

Matulis, D. 2016. Selective precipitation of proteins. Curr. Protoc. Protein Sci. 83:4.5.1-4.5.37. (Year: 2016).*
International Search Report dated Jun. 19, 2020, for related PCT application No. PCT/US2020/013139.

* cited by examiner

*Primary Examiner* — Katherine Zalasky McDonald
(74) *Attorney, Agent, or Firm* — Fish IP Law, LLP

(57) ABSTRACT

Compositions of the inventive concept provide a therapeutic protein with less than 2% contamination by the therapeutic protein in denatured form. Such compositions provide enhanced specific activity and improved stability on storage and/or in serum than corresponding therapeutic protein preparations resulting from conventional isolation methods.

8 Claims, No Drawings ously in liquid formulations), and/or reduced serum half-life
THERAPEUTIC PROTEIN COMPOSITIONS AND METHODS This application claims the benefit of U.S. Provisional Patent Application No. 62/903,659 filed on Sep. 20, 2019. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is therapeutic proteins, specifically therapeutic proteins isolated from blood or blood products.

BACKGROUND

The background description includes information that may be useful in understanding the present invention. It is not an admission that any of the information provided herein is prior art or relevant to the presently claimed invention, or that any publication specifically or implicitly referenced is prior art.

A variety of proteins are currently isolated from human blood products for therapeutic application. Examples of such proteins include albumin, immunoglobulins, alpha-1 antitrypsin, can various clotting factors. These therapeutic proteins are often used in large amounts and high concentrations. Albumin is used at high concentrations (up to 25% by weight) to restore blood volume in surgical, trauma, and burn patients. Immunoglobulin preparations (which typically contain about 10% by weight IgG) are used as immunomodulating agents to treat a wide range of diseases and conditions, and in addition to providing support for a weakened immune response can act by modulating complement activity, suppressing idiotypic antibodies, saturating macrophage Fc receptors, and suppressing of a variety of inflammatory mediators. Weekly infusion with alpha-1 antitrypsin (at about 60 mg/kg body weight) is used to treat or slow the progression of genetic disease associated with alpha-1 antitrypsin deficiency. Clotting factors (such as factor VIII, factor IX, von Willebrand factor, and other components of the clotting cascade) find use in treating hemophilia, and are provided in concentrated form in order to permit treatment by simple injection.

Due to the quantities required such therapeutic proteins are isolated from blood products (such as plasma) using scalable processes, typically a series of steps that can include precipitation, filtration, resolubilization, and treatment with chromatography media. The high degree of purity required generally necessitates the use of multiple separation steps. Typically, Cohn fractionation of serum is used, which involves a series of precipitation steps resulting from the stepwise addition of alcohol. Such extensive processing, however, can result in the accumulation of denatured forms of the therapeutic protein in the purified fractions. Such denaturation can lead to adverse reactions upon administration, reduced activity, reduced half-life on storage (particularly in liquid formulations), and/or reduced serum half-life following administration.

Thus, there is still a need for therapeutic protein preparation with minimal contamination and little to no denatured protein content.

SUMMARY OF THE INVENTION

The inventive subject matter provides compositions including a therapeutic protein that have been processed in such a manner as to have a low content of denatured therapeutic protein and/or other contaminants. Such compositions provide high specific activity and/or stability relative to corresponding preparation of therapeutic protein generated by conventional processes.

Compositions of the inventive concept include a therapeutic protein isolated from blood product (such as a modified cryo-poor plasma), where the therapeutic protein is present as a native form and a denatured form, and where the denatured form provides from about 0.01% to about 1%, 2%, 3%, 4%, or 5% of either the total amount of therapeutic protein or the native form of the therapeutic protein. In some embodiments the therapeutic protein is exposed to a precipitant during isolation. In some embodiments the therapeutic protein is alpha-1 antitrypsin, and the composition is greater than 90% inhibitory when tested with active-site titrated porcine pancreatic trypsin using N-benzoyl-L-arginine-para-nitroanilide hydrochloride (L-BAPNA) as substrate. In some embodiments the therapeutic protein is that of an immunoglobulin, and has an in vivo half-life following administration that is at least 5%, 10%, 15%, 20%, or 25% greater than an immunoglobulin fraction prepared using Cohn fractionation. In some embodiments the therapeutic protein is albumin colorless at a concentration of at least 4%, 5%, 8%, 10%, 15%, 20%, or 25%.

Another embodiment of the inventive concept is method of preparing a therapeutic protein composition as described above, by thawing frozen plasma at a temperature of from about 1° C. to about 6° C. in the presence of a precipitant to generate a modified cryoprecipitate and a modified cryo-poor plasma, separating the modified cryoprecipitate from the modified cryo-poor plasma, applying the modified cryo-poor plasma to a chromatography media without an intervening precipitation or significant dilution step to produce an unbound fraction and a bound fraction, and recovering a therapeutic protein that has only from about 0.01% to about 5% denatured therapeutic protein from either the unbound fraction or the bound fraction. Suitable precipitants include organic acids, salts of organic acids (such as sodium citrate), inorganic salts, and hydrophilic polymers.

Another embodiment of the inventive concept is a method of preparing a therapeutic protein composition as described above by adding a nonvolatile precipitant to a blood product to provide a precipitant concentration that does not result in the formation of a precipitate to form an intermediate solution, removing water from the intermediate solution while retaining the precipitant until a target precipitating concentration of the precipitant is reached to generate a precipitate and a supernatant, separating the precipitate from the supernatant, and recovering a therapeutic protein that includes from about 0.01% to about 1% denatured therapeutic protein from either the supernatant or the precipitate. Suitable precipitants include organic acids, salts of organic acids (such as sodium citrate), inorganic salts, and hydrophilic polymers. Water can be removed by evaporation (e.g. under reduced pressure) or by ultrafiltration. In some embodiments the therapeutic protein is recovered from the supernatant. In some embodiments the therapeutic protein is recovered from the precipitate.

Various objects, features, aspects and advantages of the inventive subject matter will become more apparent from the following detailed description of preferred embodiments, along with the accompanying drawing figures in which like numerals represent like components.

DETAILED DESCRIPTION

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Embodiments of the inventive concept provide therapeutic protein compositions with a low content of denatured therapeutic protein and other contaminants. The resulting composition provides the therapeutic proteins in a state that more closely resembles their state in vivo (e.g. prior to being subjected to purification techniques). Such therapeutic protein preparations demonstrate higher specific activities, extended stability, and/or prolonged in vivo half life following administration when compared to corresponding preparations resulting from prior art methods.

This is achieved, at least in part, by utilizing preparative methods that scrupulously avoid protein denaturation. Such methods, for example, can eliminate the use of denaturing organic solvents (e.g. alcohols, ketones, etc.), utilize process steps that minimize the local concentration of precipitating agents, use careful mixing to avoid the production of foam or froth, and/or avoiding or minimizing the use of denaturing precipitants (such as organic solvents). Similarly, such process steps can avoid extremes of pH (for example, maintaining a pH between about 6.5 and about 8.5, or a pH from about 6.8 to about 7.5) and/or extremes of temperature (e.g. maintaining a temperature of about 4° C. to 8° C., or a temperature of about 18° C. to about 25° C. throughout processing). Nonexclusive examples of such methods are provided below.

The source material for the vast majority of blood products is frozen plasma obtained from commercial collection centers. Slowly thawing this material at low temperature (typically from 1 to 6° C.) generates an intermediate blood product that contains precipitated proteins (i.e. cryoprecipitate or "cryo") and a protein-rich supernatant (cryo-poor plasma). Cryoprecipitate includes some of the fibrinogen content of the source plasma, as well as clotting factors and fibrin. Cryo-poor plasma is rich in cold-soluble proteins and is frequently used as a source of pharmaceutical proteins.

Cryo-poor plasma can have a protein content and/or denatured protein content that renders it unsuitable for direct application to conventional chromatographic separations without an intervening dilution or processing step. Surprisingly, the Inventors have found that the inclusion of a low concentration of a precipitant (i.e. a concentration that does not result in observable precipitation when applied to serum and/or plasma) in the thawing process can alter the protein distribution between cold-soluble and cold-insoluble fractions in the resulting preparation. The resulting modified cryo-poor plasma has been found to have a protein content that permits direct application to chromatography media (e.g. size exclusion media, ion exchange media, hydrophobic interaction media, affinity media, mixed-mode chromatography media, etc.) without intervening dilution and/or precipitation steps. This advantageously minimizes process steps, each of which provides unwanted opportunities for denaturation. Such chromatography steps can be performed while maintaining a low temperature (e.g. from 4° C. to 8° C.) similar or identical to that used in the initial thawing step, in order to reduce the chance of protein denaturation. Similarly, pH can be held constant or controlled within a restricted range (e.g. pH 6 to pH 8, pH 6.5 to 7.8, pH 6.8 to 7.2) during these steps in order to minimize denaturation.

In a preferred embodiment of the inventive concept the chromatography media is an affinity media. This advantageously both simplifies and reduces the time and materials required for plasma processing time. In addition, reduction in the number of processing steps can reduce the degree to which sensitive protein species are denatured, resulting in improved stability on storage, improved in vivo half life following administration, and/or improved specific activity.

The inventive concept also provides compositions and methods in which a non-volatile precipitant (e.g. a sulfate salt, a phosphate salt, a salt of an organic acid, and or a soluble polymer) is introduced to a blood product containing one or more target proteins and one or more contaminating proteins. In some embodiments the precipitant is provided in an amount or a concentration that does not result in the formation of a visible precipitate. Water is then removed from the resulting reaction mixture to increase the concentration of both protein and precipitant simultaneously. When the protein concentration and precipitant concentration reach the desired target values a protein precipitate forms, and is subsequently separated from the supernatant fraction. Mixing with the precipitant and separation of precipitate and supernatant fractions can be performed at a constant temperature or within a restricted temperature range (e.g. 15° C. to 25° C., 18° C. to 22° C.) in order to reduce denaturation. Similarly, pH can be held constant or controlled within a restricted range (e.g. pH 6 to pH 8, pH 6.5 to 7.8, pH 6.8 to 7.2) during these steps in order to minimize denaturation.

Depending on the nature of the target protein and the precipitant the target protein can be present in the precipitate or in the supernatant fraction. Since the protein concentration is increased as the precipitant concentration increases during this process the distribution of proteins between the precipitate and supernatant fractions is different and distinct from that produced in conventional precipitation processes in which protein concentration is decreased or at best maintained as precipitant concentration increases. In some embodiments a supernatant obtained from such a precipitation process can be subjected to additional solvent (i.e. water) removal to further increase protein and precipitant concentration and generate a second precipitate and second supernatant fraction.

Simultaneously increasing protein concentration while increasing precipitant concentration in this fashion increases the efficiency of precipitation, providing for increased yields of target proteins. In addition, initial introduction of the precipitant at concentrations that do not yield a visible precipitate precludes the formation of unwanted protein precipitants due to localized high concentrations of precipitant (as found on precipitant addition in conventional processes), decreasing the chance of undesirable protein denaturation and improving the specific activity of target proteins recovered from such processes.

As noted above, in embodiments of the inventive concept precipitants are selected to be nonvolatile (i.e. having a higher vapor pressure than water of the aqueous solution of protein under the current ambient condition). The amount of precipitant used can vary depending upon the nature of the precipitant. Suitable precipitants are preferably nondenaturing, and can include organic acids and salts of organic acids (e.g. sodium citrate), inorganic salts (e.g. ammonium sulfate, sodium sulfate, sodium chloride), and hydrophilic polymers (e.g. PEG, dextran, etc.). For example, if an organic salt such as sodium citrate is used it can be provided at concentrations ranging from about 0.1%, 0.2%, 0.5%, 1%, 2%, 3%, 4%, 5%, 6%, 7%, 8%, 9%, 10%, 12%, 15%, or less than about 20% (w/v). Similarly, if an inorganic salt such as ammonium sulfate is used it can be provided at concentrations ranging from about 0.1%, 0.2%, 0.5%, 1%, 2%, 3%, 4%, 5%, 6%, 7%, 8%, 9%, 10%, 12%, 15%, or less than about 20% (w/v). If a hydrophilic polymer such as PEG is used it can be provided at concentrations ranging from about 0.01%, 0.02%, 0.05%, 0.1%, 0.2%, 0.5%, 0.7%, 1%, 1.5%, 2%, 2.5%, 3%, 4%, 5%, 7%, or less than about 10% (w/v).

Water can be removed from an aqueous solution of proteins containing a precipitant by any suitable method. The method used can depend on the nature of the precipitant. For example, if the precipitant is a hydrophilic polymer filtration (e.g. ultrafiltration, diafiltration) utilizing a membrane with a molecular weight cutoff that is less than that of the molecular weight of the hydrophilic polymer can be used to remove water from the aqueous solution. In another embodiment, evaporation (at ambient pressure or at reduced pressure) can be used to remove water from the aqueous solution.

In a preferred embodiment of the inventive concept the therapeutic protein so obtained as a result of treatment of a blood product. Suitable blood products include serum plasma, cryo-poor plasma, a modified cryo-poor plasma as described above, resolubilized cryoprecipitate, and modified resolubilized cryoprecipitate as described above. In some embodiments the blood product can have been through various process steps (e.g. dilution, pH adjustment, addition of protease inhibitors, addition of anticoagulants, precipitation, etc.) prior to being introduced to a method of the inventive concept.

In some embodiments of the inventive concept, a supernatant or a precipitate generated by a method of the inventive concept can be further processed to recover one or more target proteins and/or remove undesirable contaminants. In such embodiments a precipitate generated by the method can be redissolved prior to the additional processing. Suitable additional processing steps include further water removal from a supernatant, conventional precipitation by addition of precipitating amounts of a precipitant, and/or chromatography (e.g. using ion exchange, hydrophobic interaction, affinity, mixed-mode, and or size exclusion chromatography media).

Chromatography media utilized in such additional processing can have any suitable formulation and configuration. Suitable media can be formulated for size exclusion, ion exchange, hydrophobic interaction, affinity, and/or mixed mode separations. Suitable media can be provided as porous granules or beads, non-porous granules or beads, filters, fibers, and/or porous membranes. Structural portions of chromatography media can be based on any suitable materials. Examples include but are not limited to polysaccharides (such as cross-lined dextran), synthetic polymers, and/or inorganic materials (such as hydroxyapatite). Chromatography media can be provided in any suitable geometry. Suitable geometries include open or sealed chromatography columns, radial chromatography columns, cartridges, membrane housings, etc.

In an example of a method of the inventive concept, a blood product (such as plasma) is obtained and blended with an equivalent volume of 8% (w/v) sodium citrate with rapid stirring, to form an aqueous protein solution with a non-precipitating sodium citrate concentration of 4% (w/v). The aqueous protein solution is transferred to a sealed container and the air pressure reduced to below that of the vapor pressure of water at the ambient temperature, resulting in the rapid evaporation of water from the solution. In some embodiments a small amount of air is continually bled into the sealed container during this process to prevent equilibration of water vapor within the sealed chamber. Water is removed until the volume of the aqueous solution is reduced to bring the sodium citrate concentration to between about 10% and 12% while increasing the protein concentration, resulting in the formation of a visible precipitate. The precipitate can then be separated from the supernatant fraction, for example by filtration or by centrifugation. Such separation can be performed at ambient or reduced pressure.

In another example of a method of the inventive concept a blood product (such as plasma) is obtained and blended with an equivalent volume of 2% (w/v) polyethylene glycol (PEG) having a mean molecular weight of 5 kD using rapid stirring, to form an aqueous protein solution with a non-precipitating PEG concentration of 1% (w/v). The aqueous protein solution is subjected to ultrafiltration using a non-fouling membrane having a 3 kD molecular weight cutoff, resulting in the rapid removal of water and other low molecular weight species from the solution while retaining the precipitant. Ultrafiltration is continued until the volume of the aqueous solution is reduced to about 25% of the original volume of the aqueous protein solution, bringing the PEG concentration to about 4% w/v while increasing the protein concentration and resulting in the formation of a visible precipitate. The precipitate can then be separated from the supernatant fraction, for example by filtration or by centrifugation.

A variety of pharmaceutically useful proteins can be obtained from methods of the inventive concept at high yield, specific activity, purity, in vitro stability, and/or in vivo stability. Such proteins include fibrinogen, factor VII, factor VIII, factor IX, factor XIII, von Willebrand factor, fibronectin, immunoglobulins, alpha-1 antitrypsin, protein C, protein S, C1 esterase inhibitor, antithrombin 3, thrombin, and/or albumin.

As noted above, therapeutic proteins found in compositions of the inventive concept have a low content of denatured therapeutic protein. The portion of therapeutic protein that is in a denatured state following application of a method of the inventive concept to a suitable starting material can range from about 0.01% to about 1%, 2%, 3%, 4%, 5%, 8%, or 10% of the total therapeutic protein content or of the native therapeutic protein content of the mixture. The therapeutic proteins so produced can have a high degree of storage stability and/or stability in vivo following administration and/or can have high specific activity, relative to corresponding therapeutic protein preparation made using conventional methods (e.g. Cohn fractionation). For example, immunoglobulin preparation of the inventive concept can have significantly greater (e.g. at least 10% greater) shelf life and/or in vivo half life following administration than corresponding immunoglobulin preparations manufactured by conventional Cohn fractionation (i.e. ethanol precipitation). Similarly, alpha-1 antitrypsin preparations of the inventive concept can be greater than 90% inhibitory when tested with active-site titrated porcine pancreatic trypsin using N-benzoyl-L-arginine-para-nitroanilide hydrochloride (L-BAPNA) as a substrate.

Similarly, contaminants (e.g. bilirubin, fatty acids, etc.) can be removed to a very high degree while retaining from 90% to 99.99% of the therapeutic protein in active, native conformation, yielding protein solutions that are colorless or essentially colorless at high protein concentrations (e.g. 10 $mgmL^{-1}$ or greater). This can be particularly useful for albumin, as such a reduction in contaminants can result in a concomitantly increased capacity for adsorption of undesirable molecules, such as circulating amyloid plaque materials and/or small organic molecules (e.g. therapeutic drugs, drugs of abuse, drug metabolites, etc.) by this protein when applied therapeutically.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of preparing a composition comprising a therapeutic protein, comprising:
    obtaining a blood product;
    adding a nonvolatile precipitant to the blood product to provide a precipitant concentration that does not result in the formation of a precipitate to form a first intermediate solution;
    removing water from the first intermediate solution while retaining the precipitant until a target precipitating concentration of the precipitant is reached to generate a precipitate and a supernatant;
    separating the precipitate from the supernatant; and
    recovering a therapeutic protein comprising from 0.01% to 5% denatured therapeutic protein from either the supernatant or the precipitate.

2. The method of claim 1, wherein the precipitant is selected from the group consisting of an organic acid, a salt of an organic acid, an inorganic salt, and a hydrophilic polymer.

3. The method of claim 1, wherein the precipitant is sodium citrate.

4. The method of claim 1, wherein water is removed by evaporation.

5. The method of claim 4, wherein evaporation is performed under reduced pressure.

6. The method of claim 1, wherein the precipitant is the hydrophilic polymer and water is removed by ultrafiltration.

7. The method of claim 1, wherein the therapeutic protein is recovered from the supernatant.

8. The method of claim 1, wherein the therapeutic protein is recovered from the precipitate.

* * * * *